(12) United States Patent
Gotou et al.

(10) Patent No.: US 11,420,923 B2
(45) Date of Patent: Aug. 23, 2022

(54) METHOD FOR PRODUCING ALPHA-FLUOROACRYLIC ACID

(71) Applicant: DAIKIN INDUSTRIES, LTD., Osaka (JP)

(72) Inventors: Akihiro Gotou, Osaka (JP); Yosuke Kishikawa, Osaka (JP); Naoyuki Hoshiya, Osaka (JP); Makoto Matsuura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/253,856

(22) PCT Filed: Jun. 21, 2019

(86) PCT No.: PCT/JP2019/024848
§ 371 (c)(1),
(2) Date: Dec. 18, 2020

(87) PCT Pub. No.: WO2019/245048
PCT Pub. Date: Dec. 26, 2019

(65) Prior Publication Data
US 2021/0269383 A1 Sep. 2, 2021

(30) Foreign Application Priority Data
Jun. 22, 2018 (JP) .............................. JP2018-119353

(51) Int. Cl.
*C07C 51/145* (2006.01)
*C07C 67/36* (2006.01)
*B01J 31/22* (2006.01)
*B01J 31/24* (2006.01)

(52) U.S. Cl.
CPC ......... *C07C 51/145* (2013.01); *B01J 31/2234* (2013.01); *B01J 31/2295* (2013.01); *B01J 31/24* (2013.01); *C07C 67/36* (2013.01); *B01J 2231/49* (2013.01); *B01J 2531/824* (2013.01)

(58) Field of Classification Search
None
See application file for complete search history.

(56) References Cited

U.S. PATENT DOCUMENTS

2016/0318842 A1  11/2016  Gotou et al.

FOREIGN PATENT DOCUMENTS

| JP | 2005-325042 | 11/2005 |
| JP | 2008-105956 | 5/2008 |
| JP | 2015-143199 | 8/2015 |
| WO | 2015/099154 | 7/2015 |

OTHER PUBLICATIONS

Machine translation of JP2015143199 (JP '199, published on Aug. 6, 2015) (Year: 2015).*
"Palladium(II)acetylacetonate", downloaded from https://pubchem.ncbi.nlm.nih.gov/compound/Palladium_II_-acetylacetonate on Dec. 16, 2021 (Year: 2021).*
"Tris(dibenzylideneacetone)dipalladium(0)", downloaded from https://pubchem.ncbi.nlm.nih.gov/compound/Tris_dibenzylideneacetone_dipalladium_0on Dec. 17, 2021 (Year: 2021).*
"Palladium, bis[(1,2,5,6-n)-1,5-cyclooctadiene]", obtained from registry number search in SciFinder® on Dec. 17, 2021 (Year: 2021).*
"12131-44-1", downloaded from https://pubchem.ncbi.nlm.nih.gov/substance/354276413 on Dec. 16, 2021. (Year: 2021).*
Machine translation of JP2008105956 (JP '956, published on May 8, 2008) (Year: 2008).*
"Allylpalladium chloride dimer", downloaded from https://pubchem.ncbi.nlm.nih.gov/compound/Allylpalladium-chloride-dimer on Dec. 16, 2021 (Year: 2021).*
International Search Report dated Sep. 17, 2019 in International (PCT) Application No. PCT/JP2019/024848.
Wu et al., "A General and Efficient Palladium-Catalyzed Alkoxycarbonylation of Phenols to Form Esters through in Situ Formed Aryl Nonaflates", Chemistry—A European Journal, 2012, vol. 18, No. 13, pp. 3831-3834.
Extended European Search Report dated Feb. 15, 2022 in European Patent Application No. 19821778.8.

* cited by examiner

*Primary Examiner* — Amy C Bonaparte
(74) *Attorney, Agent, or Firm* — Wenderoth, Lind & Ponack, L.L.P.

(57) ABSTRACT

An object of the present invention is to provide a novel method for producing an α-fluoroacrylic acid ester compound.

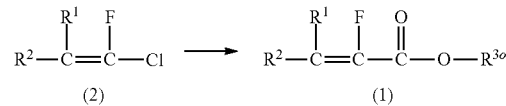

This problem is solved by a method for producing a compound represented by formula (1), wherein $R^1$ and $R^2$ are identical or different, and each represents an alkyl group or the like; and $R^3$ is an alkyl group or the like, the method comprising step A of reacting a compound represented by formula (2) with $R^3$—OH (3) and carbon monoxide in the presence of palladium, a double bond-containing compound (α), a diphosphine compound (β), and a base, to obtain the compound represented by formula (1) above.

8 Claims, No Drawings

METHOD FOR PRODUCING ALPHA-FLUOROACRYLIC ACID

TECHNICAL FIELD

The present invention relates to a method for producing an α-fluoroacrylic acid compound.

BACKGROUND ART

α-Fluoroacrylic acid compounds are useful as synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

Of α-fluoroacrylic acid compounds, a conventional method proposed for producing an α-fluoroacrylic acid ester at a high yield is, for example, a method for producing a compound represented by the following formula (1):

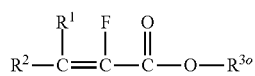
(1)

(wherein
$R^1$ and $R^2$ are identical or different, and each represents an alkyl group, a fluoroalkyl group, an aryl group optionally having one or more substituents, a halogen atom, or a hydrogen atom;
$R^{3o}$ is a hydrogen atom or $R^3$; and
$R^3$ is an alkyl group, a fluoroalkyl group, or an aryl group optionally having one or more substituents),
the method comprising
step A of reacting a compound represented by the following formula (2):

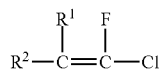
(2)

(wherein the symbols in the formula are as defined above) with carbon monoxide and an alcohol represented by the following formula (3):

$$R^3\text{—OH} \quad (3)$$

(wherein the symbol in the formula is as defined above)
in the presence of a base and a transition metal complex catalyst containing a diphosphine compound having, on each phosphorus atom, at least one substituent selected from the group consisting of alkyl and cycloalkyl groups to obtain the compound represented by formula (1) above (Patent Literature (PTL) 1).

CITATION LIST

Patent Literature

PTL 1: JP2015-143199A

SUMMARY OF INVENTION

Technical Problem

However, further novel production methods are always in demand.

In particular, it would be beneficial to provide a method that is capable of producing an α-fluoroacrylic acid ester compound at a high starting material conversion and high yield by using a small amount of a catalyst.

Solution to Problem

The present inventors found that a compound represented by formula (1), i.e., an α-fluoroacrylic acid ester compound, or a salt thereof:

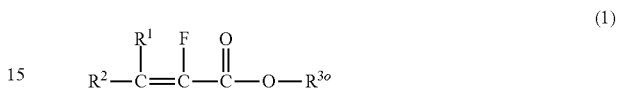
(1)

wherein
$R^1$ and $R^2$ are identical or different, and each represents an alkyl group, a fluoroalkyl group, an aryl group optionally having one or more substituents, a halogen atom, or a hydrogen atom;
$R^{3o}$ is a hydrogen atom or $R^3$; and
$R^3$ is an alkyl group, a fluoroalkyl group, or an aryl group optionally having one or more substituents,
is obtained at a high starting material conversion and high yield by reacting a compound represented by formula (2):

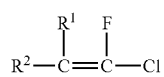
(2)

wherein the symbols in the formula are as defined above, with carbon monoxide and an alcohol represented by formula (3):

$$R^{3o}\text{—OH} \quad (3)$$

wherein the symbol in the formula is as defined above, in the presence of
palladium,
a double bond-containing compound (α) represented by formula (α):

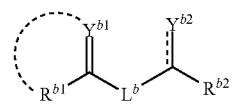
(α)

wherein
$R^{b1}$ is a hydrogen atom or a hydrocarbon group,
$R^{b2}$ is a hydrogen atom or a hydrocarbon group,
$Y^{b1}$ is =O or =CH—$R^{yb1}$,
$Y^{b2}$ is —H, =O, —CH$_2$$R^{yb2}$, or =CH—$R^{yb2}$,
$R^{yb1}$ is a hydrogen atom or a hydrocarbon group,
$R^{yb2}$ is a hydrogen atom or a hydrocarbon group,
or
$R^{b1}$ and $Y^{b1}$, taken together with the adjacent carbon atom, may form an aromatic hydrocarbon ring,
$L^b$ is a bond, $C_{1-3}$ alkanediyl optionally having one or more side chains, or —C(=O)—,
or
$R^{yb1}$ and $R^{yb2}$ may be linked to each other to form -$L^y$-, wherein $L^y$ is linear $C_{1-3}$ hydrocarbon diyl optionally having one or more side chains, wherein one of the side chains in $L^b$
(1) may be linked to one of the side chains in $L^y$ to form linear $C_{1-2}$ hydrocarbon diyl, or
(2) may be linked to $R^{b1}$ to form $C_{3-4}$ alkanediyl,
a diphosphine compound (β) having, on each phosphorus atom, at least one substituent selected from the group consisting of alkyl and cycloalkyl groups, and
a base, with the proviso that the palladium, taken together with the double bond-containing compound (α) or the diphosphine compound (β), or with both, may form a palladium complex (A). The present invention has thus been completed.

More specifically, the present invention encompasses the following embodiments.

Item 1. A method for producing a compound represented by formula (1) or a salt thereof:

  (1)

wherein
$R^1$ and $R^2$ are identical or different, and each represents an alkyl group, a fluoroalkyl group, an aryl group optionally having one or more substituents, a halogen atom, or a hydrogen atom;
$R^{3o}$ is a hydrogen atom or $R^3$; and
$R^3$ is an alkyl group, a fluoroalkyl group, or an aryl group optionally having one or more substituents,
the method comprising step A of reacting a compound represented by formula (2):

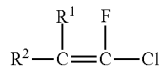  (2)

wherein the symbols in the formula are as defined above, with carbon monoxide and an alcohol represented by formula (3):

$R^3$—OH  (3)

wherein the symbol in the formula is as defined above, in the presence of
palladium,
a double bond-containing compound (α) represented by formula (α):

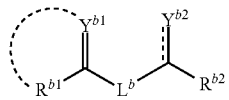  (α)

wherein
$R^{b1}$ is a hydrogen atom or a hydrocarbon group,
$R^{b2}$ is a hydrogen atom or a hydrocarbon group,
$Y^{b1}$ is =O or =CH—$R^{yb1}$,
$Y^{b2}$ is =H, =O, —$CH_2$—$R^{yb2}$, or =CH—$R^{yb2}$,
$R^{yb1}$ is a hydrogen atom or a hydrocarbon group,
$R^{yb2}$ is a hydrogen atom or a hydrocarbon group,
or
$R^{b1}$ and $Y^{b1}$, taken together with the adjacent carbon atom, may form an aromatic hydrocarbon ring, $L^b$ is a bond, $C_{1-3}$ alkanediyl optionally having one or more side chains, or —C(=O)—,
or
$R^{yb1}$ and $R^{yb2}$ may be linked to each other to form -$L^y$-, wherein $L^y$ is linear $C_{1-3}$ hydrocarbon diyl optionally having one or more side chains,
wherein one of the side chains in $L^b$
(1) may be linked to one of the side chains in $L^y$ to form linear $C_{1-2}$ hydrocarbon diyl, or
(2) may be linked to $R^{b1}$ to form $C_{3-4}$ alkanediyl,
a diphosphine compound (β) having, on each phosphorus atom, at least one substituent selected from the group consisting of alkyl and cycloalkyl groups, and
a base, with the proviso that, in the reaction, the palladium, taken together with the compound represented by formula (2), the double bond-containing compound (α), the diphosphine compound (β), or carbon monoxide, or with one or more of these, may form a palladium complex (A),
to obtain the compound represented by formula (1) or a salt thereof.

Item 2. The method according to Item 1, wherein $R^1$ and $R^2$ each represent a hydrogen atom.
Item 3. The method according to Item 1 or 2, wherein $R^{b1}$ is a hydrogen atom or an alkyl group.
Item 4. The method according to any one of Items 1 to 3, wherein $R^{b2}$ is a hydrogen atom or an alkyl group.
Item 5. The method according to any one of Items 1 to 4, wherein $R^{yb1}$ is an aryl group.
Item 6. The method according to any one of Items 1 to 5, wherein $R^{yb2}$ is a hydrogen atom or an aryl group.
Item 7. The according to any one of Items 1 to 6, wherein
$Y^{b1}$ is =O,
$Y^{b2}$ is =O, and
$L^b$ is methanediyl optionally having a side chain.
Item 8. The method according to any one of Items 1 to 7, wherein
$Y^{b1}$ is =CH—$R^{yb1}$,
$Y^{b2}$ is =CH—$R^{yb2}$, and
$L^b$ is a bond, —C(=O)—, methanediyl, or 1,2-ethanediyl.
Item 9. The method according to any one of Items 1 to 8, wherein $R^{b1}$ and $Y^{b1}$, taken together with the adjacent carbon atom, form an aromatic hydrocarbon ring,
$Y^{b2}$ is =CH—$R^{yb2}$,
$L^b$ is a bond, and
$R^{yb2}$ is an alkyl group.
Item 10. The method according to any one of Items 1 to 9, wherein $R^{b1}$ is a hydrogen atom,
$Y^{b1}$ is =CH—$R^{yb1}$,
$Y^{b2}$ is a hydrogen atom, and
$L^b$ is a bond.
Item 11. The method according to any one of Items 1 to 10, wherein the base is an amine.
Item 12. The method according to any one of Items 1 to 11, wherein step A is performed at a temperature of 20° C. or higher.

Advantageous Effects of Invention

The present invention provides a novel method for producing an α-fluoroacrylic acid ester compound.
In particular, according to the production method of the present invention, an α-fluoroacrylic acid ester compound can be suitably obtained at a high starting material conversion and a high yield by using a small amount of catalyst.

DESCRIPTION OF EMBODIMENTS

1. Terms

The steps, treatments, or operations described in the present specification may be performed at room temperature, unless otherwise specified.

In the present specification, room temperature can mean a temperature in the range of 10 to 40° C.

In the present specification, the term "$C_{n\text{-}m}$" (wherein n and m each represent a number) indicates that the number of carbon atoms is n or more and m or less, as a person skilled in the art would usually understand.

In the present specification, examples of "hydrocarbon group" include aliphatic hydrocarbon groups optionally substituted with at least one aromatic hydrocarbon group (e.g., benzyl group) and aromatic hydrocarbon groups optionally substituted with at least one aliphatic hydrocarbon group, unless otherwise specified.

In the present specification, the "aromatic hydrocarbon group" may be referred to as an "aryl group."

In the present specification, unless otherwise specified, examples of the "aromatic hydrocarbon group (aryl group)" include $C_{6\text{-}14}$ aromatic hydrocarbon groups (aryl groups). Specific examples include a phenyl group, a naphthyl group, a phenanthryl group, an anthryl group, and a pyrenyl group.

In the present specification, unless otherwise specified, the "aliphatic hydrocarbon group" may be referred to as a linear, branched, or cyclic aliphatic hydrocarbon group, or a combination thereof.

In the present specification, unless otherwise specified, the "aliphatic hydrocarbon group" may be referred to as a saturated or unsaturated aliphatic hydrocarbon group.

In the present specification, examples of the "aliphatic hydrocarbon group" include alkyl groups, alkenyl groups, alkynyl groups, cycloalkyl groups, cycloalkenyl groups, and cycloalkadienyl groups, unless otherwise specified.

In the present specification, examples of "alkyl groups" include $C_{1\text{-}6}$ alkyl groups, such as methyl, ethyl, propyl (e.g., n-propyl and isopropyl), butyl (e.g., n-butyl, isobutyl, sec-butyl, tert-butyl), pentyl (e.g., pentyl and neopentyl), and hexyl.

In the present specification, the "fluoroalkyl group" refers to an alkyl group in which at least one hydrogen atom is replaced by a fluorine atom. The "fluoroalkyl group" includes perfluoroalkyl groups. The "perfluoroalkyl group" refers to an alkyl group in which all hydrogen atoms are replaced by fluorine atoms.

In the present specification, examples of "alkenyl groups" include linear or branched $C_{1\text{-}10}$ alkenyl groups, unless otherwise specified.

Specific examples include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In the present specification, examples of "alkynyl groups" include linear or branched $C_{2\text{-}6}$ alkynyl groups, unless otherwise specified.

Specific examples include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In the present specification, examples of "$C_{1\text{-}3}$ hydrocarbon diyl" include $C_{1\text{-}3}$ alkanediyl, $C_{2\text{-}3}$ alkynediyl, and $C_{2\text{-}3}$ alkenediyl, unless otherwise specified. In the present specification, examples of "$C_{1\text{-}3}$ alkanediyl" include methanediyl, 1,1-ethanediyl, 1,2-ethanediyl, 1,1-propanediyl, 1,3-propanediyl, and 2,2-propanediyl, unless otherwise specified.

In the present specification, the "alkoxy group" refers to alkyl-O—.

In the present specification, examples of "acyl group" include alkanoyl (i.e., alkyl-C(=O)— group).

In the present specification, examples of "ester group" include alkylcarbonyloxy (i.e., alkyl-C(=O)—O— group) and alkoxycarbonyl (i.e., alkyl-O—C(=O)— group).

In the present specification, examples of "cycloalkyl groups" include $C_{3\text{-}8}$ cycloalkyl groups, such as cyclopentyl, cyclohexyl, and cycloheptyl.

In the present specification, examples of "cycloalkenyl groups" include $C_{3\text{-}7}$ cycloalkenyl groups, such as cyclopropenyl, cyclobutenyl, cyclopentenyl, cyclohexenyl, and cycloheptenyl.

In the present specification, examples of "cycloalkadienyl groups" include $C_{4\text{-}10}$ cycloalkadienyl groups, such as cyclobutadienyl, cyclopentadienyl, cyclohexadienyl, cycloheptadienyl, cyclooctadienyl, cyclononadienyl, and cyclodecadienyl.

2. Method for Producing α-Fluoroacrylic Acid Ester Compound (1)

The method of the present invention for producing a compound represented by formula (1) or a salt thereof (in the present specification, sometimes referred to as "the α-fluoroacrylic acid compound (1)"):

(1)

wherein $R^1$ and $R^2$ are identical or different, and each represents an alkyl group, a fluoroalkyl group, an aryl group optionally having one or more substituents, a halogen atom, or a hydrogen atom;

$R^{3o}$ is a hydrogen atom or $R^3$; and $R^3$ is an alkyl group, a fluoroalkyl group, or an aryl group optionally having one or more substituents, comprises step A of reacting a compound represented by formula (2):

(2)

wherein the symbols in the formula are as defined above, with carbon monoxide and an alcohol represented by formula (3):

(3)

$$R^3\text{—OH}$$

wherein the symbol in the formula is as defined above, in the presence of palladium, a double bond-containing compound (α) represented by formula (α):

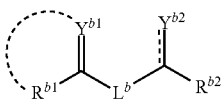

(α)

wherein
$R^{b1}$ is a hydrogen atom or a hydrocarbon group,
$R^{b2}$ is a hydrogen atom or a hydrocarbon group,
$Y^{b1}$ is =O or =CH—$R^{yb1}$,
$Y^{b2}$ is —H, =O, —CH$_2$$R^{yb2}$, or =CH—$R^{yb2}$,
$R^{yb1}$ is a hydrogen atom or a hydrocarbon group,
$R^{yb2}$ is a hydrogen atom or a hydrocarbon group,
or
$R^{b1}$ and $Y^{b1}$, taken together with the adjacent carbon atom, may form an aromatic hydrocarbon ring,
$L^b$ is a bond, $C_{1-3}$ alkanediyl optionally having one or more side chains, or —C(=O)—,
or
$R^{yb1}$ and $R^{yb2}$ may be linked to each other to form -$L^y$-, wherein $L^y$ is linear $C_{1-3}$ hydrocarbon diyl optionally having one or more side chains,
wherein one of the side chains in $L^b$
(1) may be linked to one of the side chains in $L^y$ to form linear $C_{1-2}$ hydrocarbon diyl, or
(2) may be linked to $R^{b1}$ to form $C_{3-4}$ alkanediyl,
a diphosphine compound (β) having, on each phosphorus atom, at least one substituent selected from the group consisting of alkyl and cycloalkyl groups, and
a base, with the proviso that the palladium, taken together with the double bond-containing compound (α) or the diphosphine compound (β), may form a palladium complex (A),
to obtain the compound represented by formula (1) above.

The dotted lines in the structural formulas can represent any bond or linkage, as is commonly understood by those skilled in the art. However, the absence of dotted lines in a structural formula does not necessarily mean that there is no bond or linkage. The presence or absence of a bond or linkage can be understood based on the description in the present specification. More specifically, as described above, —$R^{yb1}$ in $Y^{b1}$ can be linked to —$R^{yb2}$ in $Y^{b2}$, and, in this sense, $Y^{b1}$ can be linked to $Y^{b2}$.

Only for the sake of confirmation, when $Y^{b2}$ in formula (α) is —H, the partial structural formula on the right side of formula (α) with respect to $L^b$ represents the structure: -$L^b$-CH$_2$—$R^{b2}$, as is commonly understood by those skilled in the art.

Examples of the salts of the compounds represented by formula (1) include metal salts (e.g., sodium salts and potassium salts), ammonium salts, and imidazole salts.

2.1. α-Fluoroacrylic Acid Compound (1), Chlorofluoroethylene Compound (2), and Alcohol (3)

The symbols in formulas (1), (2), and (3) above representing the α-fluoroacrylic acid compound (1), the chlorofluoroethylene compound (2), and the alcohol (3) are explained below.

The "alkyl group" represented by $R^1$ is preferably a linear or branched $C_{1-6}$ alkyl group, more preferably a linear or branched $C_{1-5}$ alkyl group, and still more preferably a linear or branched $C_{1-4}$ alkyl group.

The "fluoroalkyl group" represented by $R^1$ is preferably a linear or branched $C_{1-6}$ fluoroalkyl group, more preferably a linear or branched $C_{1-5}$ fluoroalkyl group, and still more preferably a linear or branched $C_{1-4}$ fluoroalkyl group.

Preferable examples of the substituents of the "aryl group optionally having one or more substituents" represented by $R^1$ include fluorine, alkyl, alkoxy, acyl, ester, cyano, nitro, and fluoroalkyl. More preferable examples include a fluorine atom.

$R^1$ is preferably a hydrogen atom, a linear or branched alkyl group, or an aryl group optionally having one or more substituents, more preferably a hydrogen atom, a linear or branched $C_{1-6}$ alkyl group, or an aryl group optionally having one or more substituents, still more preferably a hydrogen atom, a linear or branched $C_{1-4}$ alkyl group, or an aryl group optionally having one or more substituents, even more preferably a hydrogen atom or an aryl group optionally having one or more substituents, and particularly preferably a hydrogen atom.

The "alkyl group" represented by $R^2$ is preferably a linear or branched $C_{1-6}$ alkyl group, more preferably a linear or branched $C_{1-5}$ alkyl group, and still more preferably a linear or branched $C_{1-4}$ alkyl group.

The "fluoroalkyl group" represented by $R^2$ is preferably a linear or branched $C_{1-6}$ fluoroalkyl group, more preferably a linear or branched $C_{1-5}$ fluoroalkyl group, and still more preferably a linear or branched $C_{1-4}$ fluoroalkyl group.

Preferable examples of the substituents of the "aryl group optionally having one or more substituents" represented by $R^2$ include fluorine, alkyl, alkoxy, acyl, ester, cyano, nitro, and fluoroalkyl. More preferable examples include a fluorine atom.

$R^2$ is preferably a hydrogen atom, a linear or branched alkyl group, or an aryl group optionally having one or more substituents, more preferably a hydrogen atom, a linear or branched $C_{1-6}$ alkyl group, or an aryl group optionally having one or more substituents, still more preferably a hydrogen atom, a linear or branched $C_{1-4}$ alkyl group, or an aryl group optionally having one or more substituents, even more preferably a hydrogen atom or an aryl group optionally having one or more substituents, and particularly preferably a hydrogen atom.

$R^1$ and $R^2$ each are particularly preferably a hydrogen atom.

$R^{3o}$ is preferably $R^3$. In the present specification, among α-fluoroacrylic acid compounds (1), a compound in which $R^{3o}$ is $R^3$ may be referred to as an "α-fluoroacrylic acid ester compound (1e)."

The "alkyl group" represented by $R^3$ is preferably a linear or branched $C_{1-6}$ alkyl group, more preferably a linear or branched $C_{1-5}$ alkyl group, and still more preferably a linear or branched $C_{1-4}$ alkyl group.

The "fluoroalkyl group" represented by $R^3$ is preferably a linear or branched $C_{1-6}$ fluoroalkyl group, more preferably a linear or branched $C_{1-5}$ fluoroalkyl group, and still more preferably a linear or branched $C_{1-4}$ fluoroalkyl group.

Preferable examples of the substituents of the "aryl group optionally having one or more substituents" represented by $R^3$ include fluorine, alkyl, alkoxy, acyl, ester, cyano, nitro, and fluoroalkyl. More preferable examples include a fluorine atom.

$R^3$ is preferably (a) a linear or branched $C_{1-6}$ alkyl group or (b) a linear or branched $C_{1-6}$ fluoroalkyl group, more preferably (a) a linear or branched $C_{1-4}$ alkyl group or (b) linear or branched $C_{1-4}$ fluoroalkyl group, still more preferably a methyl group, an ethyl group, or a linear or branched $C_{1-3}$ fluoroalkyl group, even more preferably a methyl group or an ethyl group, and particularly preferably a methyl group.

The α-fluoroacrylic acid compound (1) is preferably 2-fluoroacrylic acid methyl ester, 2-fluoroacrylic acid ethyl ester, 2-fluoroacrylic acid 2,2,2-trifluoroethyl ester, or 2-fluoroacrylic acid 1,1,1,3,3,3-hexafluoro-2-propyl ester, more preferably 2-fluoroacrylic acid methyl ester or 2-fluoroacrylic acid ethyl ester, and particularly preferably 2-fluoroacrylic acid methyl ester.

The chlorofluoroethylene compound (2) is a known compound and can be produced by a known method, or can be a commercially available product.

The alcohol (3) is preferably an alcohol represented by formula: $R^3$—OH,
wherein R is preferably a linear or branched $C_{1-6}$ alkyl group, more preferably a linear or branched $C_{1-5}$ alkyl group, and more preferably a linear or branched $C_{1-4}$ alkyl group.

In particular, when the alcohol (3) is also used to function as a solvent for the reaction of step A as described later, the alcohol (3) is preferably as described above.

The "fluoroalkyl group" represented by $R^3$ is preferably a linear or branched $C_{1-6}$ fluoroalkyl group, more preferably a linear or branched $C_{1-5}$ fluoroalkyl group, and still more preferably a linear or branched $C_{1-4}$ fluoroalkyl group.

Specifically, the alcohol (3) is preferably methanol, ethanol, trifluoroethanol, pentafluoropropanol, or hexafluoroisopropanol, and particularly preferably methanol.

It is preferable that $R^1$ be a hydrogen atom, a linear or branched alkyl group, or an aryl group optionally having one or more substituents;
$R^2$ be a hydrogen atom, a linear or branched alkyl group, or an aryl group optionally having one or more substituents; and
$R^3$ be (a) a linear or branched $C_{1-6}$ alkyl group or (b) a linear or branched $C_{1-6}$ fluoroalkyl group.

It is more preferable that
$R^1$ be a hydrogen atom, a linear or branched $C_{1-6}$ alkyl group, or an aryl group optionally having one or more substituents;
$R^2$ be a hydrogen atom, a linear or branched $C_{1-6}$ alkyl group, or an aryl group optionally having one or more substituents; and
$R^3$ be (a) a linear or branched $C_{1-4}$ alkyl group or (b) a linear or branched $C_{1-4}$ fluoroalkyl group.

It is still more preferable that
$R^1$ be a hydrogen atom, a linear or branched $C_{1-4}$ alkyl group, or an aryl group optionally having one or more substituents;
$R^2$ be more preferably a hydrogen atom, a linear or branched $C_{1-4}$ alkyl group, or an aryl group optionally having one or more substituents; and
$R^3$ be a methyl group, an ethyl group, or a linear or branched $C_{1-3}$ fluoroalkyl group.

It is even more preferable that
$R^1$ be a hydrogen atom or an aryl group optionally having one or more substituents;
$R^2$ be a hydrogen atom or an aryl group optionally having one or more substituents; and
$R^3$ be a methyl group or an ethyl group.

It is particularly preferable that
$R^1$ be a hydrogen atom;
$R^2$ be a hydrogen atom; and
$R^3$ be a methyl group.

The alcohol (3) can also function as a solvent for the reaction in step A.

The amount of the alcohol (3) used as a reaction starting material in step A is usually 1 to 500 mol, and preferably about 1.1 to 50 mol, per mole of the chlorofluoroethylene compound (2).

When the alcohol (3) is also used as a solvent for the reaction in step A, the alcohol is usually used in large excess with respect to the chlorofluoroethylene compound (2).

Specifically, when a solvent other than the alcohol is not used, the amount of the alcohol per mole of the chlorofluoroethylene compound (2) is, for example, 0.1 L or more, 0.2 L or more, 0.5 L or more, or 0.7 L or more, and 20 L or less, 10 L or less, or 5 L or less; and may be in the range of 0.1 to 20 L, in the range of 0.1 to 20 L, in the range of 0.2 to 15 L, in the range of 0.5 to 10 L, or in the range of 0.7 to 5 L.

The reaction pressure in step A is not limited and may be, for example, equal to or higher than atmospheric pressure. Step A is preferably performed in a container such as an autoclave, and carbon monoxide as a reaction starting material in step A can be introduced into the container using a gas containing carbon monoxide, such as purified carbon monoxide gas. The pressure of carbon monoxide is usually 0 to 10 MPaG, and preferably 0.5 to 5 MPaG.

2.2. Palladium Complex (A)

In the reaction in step A, palladium may form a palladium complex (A), taken together with the compound represented by formula (2), the double bond-containing compound (α), the diphosphine compound (β), or carbon monoxide; or with one or more of these.

The palladium complex (A) used in step A may preferably contain palladium and the double bond-containing compound (α).

Further, the palladium complex (A) used in step A may preferably contain palladium and the diphosphine compound (β).

Furthermore, the palladium complex (A) used in step A may preferably contain palladium, the double bond-containing compound (α), and the diphosphine compound (β).

2.2.1. Palladium

The palladium can be zero-, mono-, di-, tri-, or tetravalent.

The palladium can preferably be zero- or di-valent.

2.2.2. Double Bond-containing Compound (α)

The symbols in formula (α) above are explained below.
$R^{b1}$ is a hydrogen atom or a hydrocarbon group. $R^{b1}$ is preferably a hydrogen atom or an alkyl group, and more preferably a hydrogen atom or a methyl group.
$R^{b2}$ is a hydrogen atom or a hydrocarbon group. $R^{b2}$ is preferably a hydrogen atom or an alkyl group, and more preferably a hydrogen atom or a methyl group.
$Y^{b1}$ is =O or =CH—$R^{yb1}$, wherein $R^{yb1}$ is a hydrogen atom or a hydrocarbon group, preferably an aryl group, and more preferably a phenyl group.
$Y^{b2}$ is =O or =CH—$R^{yb2}$, wherein $R^{yb2}$ is a hydrogen atom or a hydrocarbon group, preferably an aryl group, and more preferably a phenyl group.

Alternatively, $R^{yb1}$ and $R^{yb2}$ may be linked to each other to foam -$L^y$-.

Here, -$L^y$- is linear $C_{1-3}$ hydrocarbon diyl optionally having one or more side chains, preferably linear $C_{1-2}$ alkanediyl, and more preferably 1,2-ethanediyl.

Examples of the side chains include methyl.

One of the side chains in $L^b$
(1) may be linked to one of the side chains in $L^y$ to form linear $C_{1-2}$ hydrocarbon diyl (preferably methanediyl), or
(2) may be linked to $R^{b1}$ to form $C_{3-4}$ alkanediyl (preferably linear $C_{3-4}$ alkanediyl).

The palladium complex (A) does not necessarily have to retain its form as a complex once it is introduced into the reaction system of step A.

On the other hand, the palladium complex (A) may be produced in the reaction system of step A by introducing its precursor into the reaction system of step A.

At least one member selected from the group consisting of the palladium complex (A), palladium, and the double bond-containing compound (α) may form a complex, together with the diphosphine compound (β) in the reaction system of step A.

In a preferred embodiment of the present invention,
$Y^{b1}$ is =O,
$Y^{b2}$ is =O, and
$L^b$ is methanediyl optionally having one side chain.

In another preferred embodiment of the present invention,
$Y^{b1}$ is =CH—$R^{yb1}$,
$Y^{b2}$ is =CH—$R^{yb2}$, and
$L^b$ is a bond, —C(=O)—, or 1,2-ethanediyl.

In another preferred embodiment of the present invention,
$R^{b1}$ and $Y^{b1}$, taken together with the adjacent carbon atom, form an aromatic hydrocarbon ring,
$Y^{b2}$ is =CH—$R^{yb2}$,
$L^b$ is a bond, and
$R^{yb2}$ is an alkyl group In another preferred embodiment of the present invention,
$R^{b1}$ is a hydrogen atom (—H),
$Y^{b1}$ is =CH—$R^{yb1}$,
$Y^{b2}$ is a hydrogen atom, and
$L^b$ is a bond.

Specific examples of the double bond-containing compound (α) include
(1) dione compounds, such as
1-phenylbutane-1,3-dione,
1,3-diphenylpropane-1,3-dione,
3-methyl-2,4-pentanedione,
2,2,6,6-tetramethylheptane-3,5-dione,
3,5-heptanedione,
2-acetylcyclohexanone,
2-acetylcyclopentanone,
hexane-2,4-dione,
3,3-dimethyl-2,4-pentanedione, and
2,4-pentanedione;
(2) diene compounds, such as
cycloocta-1,5-diene,
cyclohepta-1,3-diene,
cyclohepta-1,4-diene,
cyclohexa-1,3-diene,
cyclohexa-1,4-diene,
cyclopentadiene,
1,3-butadiene,
2-methyl-1,3-butadiene,
2,3-dimethyl-1,3-butadiene, and
norbornadiene; and
(3) other double bond-containing compounds, such as
trans,trans-1,5-diphenyl-1,4-pentadien-3-one,
1-propene, and
1-phenyl-1-propene.

Preferable examples of the double bond-containing compound include 2,4-pentanedione and cycloocta-1,5-diene.

The double bond-containing compound (α) may be in the form of its conjugate base.

These double bond-containing compounds (α) may be used alone, or in a combination of two or more.

In the present invention, other metals or catalysts containing other metals may be used in combination with the palladium complex (A).

The amount of the "other metals" may be usually one mole or less per mole of palladium.

The "other metals" may be, for example, at least one member selected from the group consisting of nickel, copper, iron, platinum, ruthenium, rhodium, and cobalt.

Diphosphine Compound (β)

The diphosphine compound (β) is a diphosphine compound having, on each phosphorus atom, at least one substituent selected from the group consisting of alkyl and cycloalkyl groups; preferably a diphosphine compound having, on each phosphorus atom, at least one substituent selected from the group consisting of linear or branched alkyl groups (preferably $C_{1-6}$ alkyl and more preferably $C_{1-4}$ alkyl) and cycloalkyl groups (preferably $C_{3-8}$ cycloalkyl and more preferably $C_{3-6}$ cycloalkyl); and particularly preferably, for example, a diphosphine compound having, on each phosphorus atom, at least one substituent selected from the group consisting of isopropyl and cyclohexyl.

Specific examples of the diphosphine compound (β) include
bis(dicyclohexylphosphinophenyl)ether,
1,1'-bis(dicyclohexylphosphino)ferrocene,
1,1'-bis(diisopropylphosphino)ferrocene,
1,1'-bis(di-tert-butylphosphino)ferrocene,
1,3-bis(diisopropylphosphino)propane,
1,4-bis(diisopropylphosphino)butane,
1,3-bis(dicyclohexylphosphino)propane,
1,4-bis(dicyclohexylphosphino)butane,
(1S,1S',2R,2R')-1,1'-di-tert-butyl-(2,2')-diphosphorane,
(3S,3'S,4S,4'S,11bS,11'bS)-(+)-4,4'-di-tert-butyl-4,4',5,5'-tetrahydro-3,3'-bi-3H-dinaphtho[2,1-c:1',2'-e]phosphine,
(1R,1R',2S,2S')-(+)-2,2'-di-tert-butyl-2,3,2',3'-tetrahydro-1,1'-bi-1H-isophosphenylindole,
1,2-bis(di-tert-butylphosphinomethyl)benzene,
(−)-1,2-bis-[(2R,5R)-2,5,-dimethylphosphorano]benzene,
(R)-1-[(Sp)-2-(dicyclohexylphosphino) ferrocenyl]ethyldi-tert-butylphosphine,
(Rp)-1-dicyclohexylphosphino-2-[(R)-α-(dimethylamino)-2-(dicyclohexylphosphino benzyl)]ferrocene,
(R,R)-(−)-2,3-bis(tert-butylmethylphosphino)quinoxaline, and
(R)-1-[(S)-2-(dicyclohexylphosphino)ferrocenyl]ethyl dicyclohexylphosphine.

Preferable examples of the diphosphine compound (β) include
bis(dicyclohexylphosphinophenyl)ether,
1,1'-bis(dicyclohexylphosphino)ferrocene,
1,1'-bis(diisopropylphosphino)ferrocene,
1,3-bis (diisopropylphosphino)propane,
1,4-bis(diisopropylphosphino)butane,
1,3-bis(dicyclohexylphosphino)propane,
1,4-bis(dicyclohexylphosphino)butane,
(R)-1-[(Sp)-2-(dicyclohexylphosphino) ferrocenyl]ethyldi-tert-butylphosphine,
(Rp)-1-dicyclohexylphosphino-2-[(R)-α-(dimethylamino)-2-(dicyclohexylphosphino benzyl)]ferrocene,
(R,R)-(−)-2,3-bis(tert-butylmethylphosphino)quinoxaline, and
(R)-1-[(S)-2-(dicyclohexylphosphino)ferrocenyl]ethyl dicyclohexylphosphine.

The diphosphine compound (β) may be a tetrafluoroborate (e.g., a bis(tetrafluoroborate) of diphosphine compound, such as 1,1'-bis(dicyclohexylphosphino)ferrocene bis(tetrafluoroborate) and 1,3-bis(dicyclohexylphosphino)propane bis(tetrafluoroborate)), hydrofluoric acid salt, hydrochloric acid salt, hydrobromic acid salt, hydroiodic acid salt, acetate, trifluoroacetate, methanesulfonate, trifluoromethanesulfonate, p-toluenesulfonate, or hexafluorophosphate. These salts can react with a base to give a free form of phosphine (e.g., a diphosphine compound, such as 1,1'-bis(dicyclohexylphosphino)ferrocene and 1,3-bis(dicyclohexylphosphino)propane).

Examples of the base include amines, inorganic bases, organic metal bases.

Examples of the amines include triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, 1,8-diazabicyclo[5,4,0]-7-undecene, 1,5-diazabicyclo[4,3,0]-5-nonene, and 1,4-diazabicyclo[2,2,2]octane.

Examples of the inorganic bases include lithium hydroxide, potassium hydroxide, sodium hydroxide, calcium hydroxide, lithium carbonate, sodium carbonate, potassium carbonate, sodium hydrogen carbonate, potassium hydrogen carbonate, lithium phosphate, sodium phosphate, and potassium phosphate.

Examples of the organic metal bases include organic alkali metal compounds, such as butyllithium, tert-butyllithium, phenyllithium, sodium triphenylmethyl, and sodium ethyl; organic alkali earth metal compounds, such as methylmagnesium bromide, dimethylmagnesium, phenylmagnesium chloride, phenylcalcium bromide, and bis(dicyclopentadiene)calcium; and alkoxides, such as sodium methoxide and tert-butyl methoxide.

Preferable examples of the bases include triethylamine, potassium carbonate, and potassium phosphate. More preferable examples of the bases include potassium carbonate and potassium phosphate. Particularly preferable examples of the bases include potassium phosphate.

The bases can be used alone, or in a combination of two or more.

The diphosphine compound (β) may form a coordinate bond with the palladium complex (A) or with palladium in the palladium complex (A). The coordinate bond may be formed with, for example, palladium contained in the palladium complex (A).

The number of the coordinate bonds of the diphosphine compound with palladium depends on, for example, the oxidation number of the transition metal, and is preferably, for example, one or two.

Preferable examples of the precursor of the palladium complex (A) produced in the reaction system include palladium chloride, palladium bromide, palladium iodide, palladium acetate, dichloro bis(acetonitrile) palladium (II), dichloro bis(benzonitrile) palladium (II), dichloro bis(triphenylphosphine)palladium (II), and Pd(PPh$_3$)$_4$ (Ph is phenyl).

As described above, the palladium complex (A) may be added to the reaction system as a reagent, or may be formed in the reaction system by using the precursor as described above as a starting material.

Thus, the reaction in step A may be performed by using, for example, (1) a combination of
(i) a palladium compound that contains the double bond-containing compound, and
(ii) the diphosphine compound (β);
(2) a combination of
(i) the precursor of the palladium complex (A) (i.e., a palladium compound that does not contain the double bond-containing compound),
(ii) the phosphine compound (β), and
(iii) the double bond-containing compound;
(3) a combination of
(i) a complex compound containing the precursor of the palladium complex (A) (i.e., a palladium compound that does not contain the double bond-containing compound) and the phosphine compound (β), and
(ii) the double bond-containing compound; or
(4) a combination of
(i) a complex compound containing the precursor of the palladium complex (A) (i.e., a palladium compound that does not contain the double bond-containing compound), the chlorofluoroethylene compound (2), and carbon monoxide, and
(ii) the double bond-containing compound.

Specific examples of the palladium compound that contains the double bond-containing compound include
bis(acetylacetonato)palladium (II),
tris(dibenzylidenacetone)dipalladium (0),
bis(dibenzylidenacetone)palladium (0),
bis(cycloocta-1,5-diene)palladium (0),
palladium (II) (n-cinnamyl)chloride,
allyl palladium (II) chloride, and
dichloro(cycloocta-1,5-diene)palladium (II).

Specific examples of the complex compound containing the precursor of the palladium complex (A) and the phosphine compound (β) include
[bis(dicyclohexylphosphinophenyl)ether]dichloropalladium (II),
[1,1'-bis(dicyclohexylphosphino)ferrocene]dichloropalladium (II),
[1,1'-bis(diisopropylphosphino)ferrocene]dichloropalladium (II),
[1,1'-bis(di-tert-butylphosphino)ferrocene]dichloropalladium (II),
[1,3-bis(diisopropylphosphino)propane]dichloropalladium (II),
[1,4-bis(diisopropylphosphino)butane]dichloropalladium (II),
[1,3-bis(dicyclohexylphosphino)propane]dichloropalladium (II),
[1,4-bis(dicyclohexylphosphino)butane]dichloropalladium (II),
[(1S,1S',2R,2R')-1,1'-di-tert-butyl-(2,2')-diphosphorane]dichloropalladium (II),
[(3S,3'S,4S,4'S,11bS,11'bS)-(+)-4,4'-di-tert-butyl-4,4',5,5'-tetrahydro-3,3'-bi-3H-dinaphtho[2,1-c:1',2'-e]phosphine]dichloropalladium (II),
[(1R,1R',2S,2S')-(+)-2,2'-di-tert-butyl-2,3,2',3'-tetrahydro-1,1'-bi-1H-isophosphenylindole]dichloropalladium(II),
[1,2-bis(di-tert-butylphosphinomethyl)benzene]dichloropalladium (II),
[(−)-1,2-bis-[(2R,5R)-2,5,-dimethylphosphorano]benzene]dichloropalladium (II),
[(R)-1-[(Sp)-2-(dicyclohexylphosphino)ferrocenyl]ethyl-di-tert-butylphosphine]dichloropalladium (II),
[(Rp)-1-dicyclohexylphosphino-2-[(R)-α-(dimethylamino)-2-(dicyclohexylphosphino benzyl)]ferrocene]dichloropalladium (II),
[(R,R)-(−)-2,3-bis(tert-butylmethylphosphino)quinoxaline]dichloropalladium (II), and
[(R)-1-[(S)-2-(dicyclohexylphosphino)ferrocenyl]ethyl dicyclohexylphosphine]dichloropalladium (II).

The palladium complex (A) used in step A may be in the form of a heterogeneous catalyst dispersed in or supported on a polymer such as polystyrene and polyethylene.

For the double bond-containing compound (α) and the diphosphine compound (β), those described above may also be used.

When such a heterogeneous catalyst is used, the double bond-containing compound (α) may be originally bound to the heterogeneous catalyst, or the double bond-containing compound (α) may be separately added to form a heterogeneous palladium complex (A) in which the double bond-containing compound is bound in the reaction system.

Such heterogeneous catalysts are advantageous in terms of processes such as catalyst recovery. Specific examples of the catalytic structure include the structure represented by the following chemical formula:

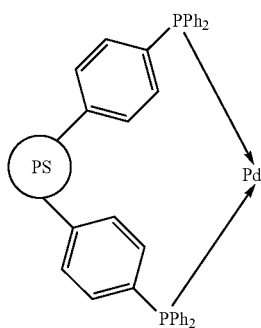

wherein PS is polystyrene, and Ph is phenyl. In this structure, the palladium atom is immobilized by a polymeric phosphine that is obtained by introducing phosphine into a crosslinked polystyrene (PS) chain.

The diphosphine compound (β) in this example is a compound in which one of the three phenyl groups of each bimolecular triphenylphosphine is bonded to a polymer chain, as shown in the following chemical formula:

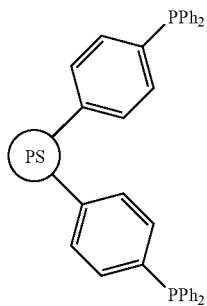

wherein PS is polystyrene and Ph is phenyl.

The palladium complex (A) used in step A may be a supported catalyst supported on a carrier. Such a supported catalyst has a cost advantage because the catalyst can be reused.

Examples of the carriers include carbon, alumina, silica-alumina, silica, barium carbonate, barium sulfate, calcium carbonate, titanium oxide, zirconium oxide, and zeolite.

The palladium complex (A) used in step A may contain at least one ligand other than "the diphosphine compound having, on each phosphorus atom, at least one substituent selected from the group consisting of alkyl and cycloalkyl groups." Examples of the ligands include chlorine ligands.

The upper limit of the amount of the palladium complex (A) is, for example, 0.05 mol, 0.01 mol, 0.005 mol, 0.002 mol, 0.001 mol, 0.00075 mol, 0.0005 mol, 0.00025 mol, 0.0001 mol, or 0.00006 mol, per mole of the chlorofluoroethylene compound (2).

In the present invention, the desired product can be obtained at a high yield as described later, even with such a small amount of catalyst.

The lower limit of the amount of the palladium complex (A) is usually 0.00001 mol, and more preferably 0.00002 mol or 0.00004 mol, per mole of the chlorofluoroethylene compound (2).

Base (C)

Step A is performed in the presence of a base.

Examples of bases used in step A include amines, inorganic bases, and organic metal bases.

Examples of amines include aliphatic amines (primary amine, secondary amine, tertiary amine), alicyclic amines (secondary amine, tertiary amine), aromatic amines (primary amine, secondary amine, tertiary amine), and heterocyclic amines; and polymers carrying amine compounds (e.g., polyallylamine, polyvinylpyridine).

Specific examples of amines include triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, 1,8-diazabicyclo[5,4,0]-7-undecene, 1,5-diazabicyclo[4,3,0]-5-nonene, and 1,4-diazabicyclo[2,2,2]octane.

Examples of inorganic bases include lithium hydroxide, potassium hydroxide, sodium hydroxide, calcium hydroxide, lithium carbonate, sodium carbonate, potassium carbonate, sodium hydrogen carbonate, and potassium hydrogen carbonate.

Examples of organic metal bases include organic alkali metal compounds, such as butyllithium, t-butyllithium, phenyllithium, sodium triphenylmethyl, and sodium ethyl; organic alkali earth metal compounds, such as methylmagnesium bromide, dimethylmagnesium, phenylmagnesium chloride, phenylcalcium bromide, and bis(dicyclopentadiene)calcium; and alkoxides, such as sodium methoxide and t-butyl methoxide.

The base used in step A may preferably be an amine.

Preferable specific examples of bases include tertiary amines (in particular, preferably aliphatic tertiary amines (e.g., triethylamine and diisopropylethylamine)), lithium hydroxide, potassium carbonate, and lithium carbonate.

More preferable specific examples of bases include triethylamine, diisopropylethylamine, potassium carbonate, and lithium carbonate.

Particularly preferable specific examples of bases include triethylamine and diisopropylethylamine.

The bases may be used alone, or in a combination of two or more.

The amount of base is usually 0.2 to 5 mol, and preferably about 0.5 to 3 mol, per mole of the chlorofluoroethylene compound (2).

Other Additives

In the production method of the present invention, other additives may be used as long as the effect of the present invention is not significantly impaired.

Preferable examples of the additives include the double bond-containing compound and conjugate bases thereof. In this case, for example, the double bond-containing compound or a conjugate base thereof may be partially used as a material of the palladium complex (A), and the rest may be used as an additive.

The additive may be more preferably, for example, a polymerization inhibitor.

Specific examples of polymerization inhibitors include dibutylhydroxytoluene (BHT), 4-methoxyphenol, hydroquinone, phenothiazine, benzoquinone, and phenothiazine.

Reaction Temperature

Step A is usually performed at a temperature of 20° C. or higher, preferably 50° C. or higher, and more preferably 80° C. or higher.

When the reaction temperature is adjusted to be within this temperature range, high starting material conversion can be achieved.

When the reaction temperature is adjusted to be within this temperature range, high yield can be achieved.

Step A is usually performed at a temperature of 150° C. or lower, preferably 120° C. or lower, and more preferably 110° C. or lower.

When the reaction temperature is adjusted to be within this temperature range, the formation of by-products can be suppressed.

Step A is usually performed at a temperature of 20 to 150° C., preferably 50 to 120° C., and more preferably 80 to 110° C.

If the temperature is excessively low, there is a tendency towards lower starting material conversion and lower yield.

In contrast, if the temperature is excessively high, the mixture obtained after the reaction in step A may contain by-products or decomposition products, which may be observed in analysis performed by the analysis method described below.

Analysis Method

After completion of the reaction, hexafluorobenzene is added as an internal standard substance, and the resulting mixture is stirred. The mixture is then allowed to stand for a period of time to precipitate the salt. The supernatant is diluted with deuterated chloroform, and subjected to quantification based on $^{19}$F-NMR integral values.

Solvent

In step A, in addition to the alcohol (3), which can also serve as a solvent, other solvent(s) may be used. In this case, the amount of the alcohol (3) can be reduced.

Examples of such solvents include non-aromatic hydrocarbon solvents, such as pentane, hexane, heptane, octane, cyclohexane, decahydronaphthalene, n-decane, isododecane, and tridecane; aromatic hydrocarbon solvents, such as benzene, toluene, xylene, tetralin, veratrole, diethylbenzene, methylnaphthalene, nitrobenzene, o-nitrotoluene, mesitylene, indene, and diphenyl sulfide; ketones, such as acetone, methyl ethyl ketone, methyl isobutyl ketone, acetophenone, propiophenone, diisobutyl ketone, and isophorone; halogenated hydrocarbon solvents, such as dichloromethane, chloroform, and chlorobenzene; ether solvents, such as diethyl ether, tetrahydrofuran, diisopropyl ether, methyl t-butyl ether, dioxane, dimethoxyethane, diglyme, phenetole, 1,1-dimethoxy cyclohexane, and diisoamyl ether; ester solvents, such as ethyl acetate, isopropyl acetate, diethyl malonate, 3-methoxy-3-methylbutyl acetate, γ-butyrolactone, ethylene carbonate, propylene carbonate, dimethyl carbonate, and α-acetyl-γ-butyrolactone; nitrile solvents, such as acetonitrile and benzonitrile; sulfoxide-based solvents, such as dimethylsulfoxide and sulfolane; and amide solvents, such as N,N-dimethylformamide, N,N-dimethylacetamide, N-methylpyrrolidone, 1,3-dimethyl-2-imidazolidinone, N,N-dimethylacrylamide, N,N-dimethylacetoacetamide, N,N-diethylformamide, and N,N-diethylacetamide.

Preferable examples of solvents include non-aromatic hydrocarbons, such as heptane, octane, and cyclohexane; aromatic hydrocarbon solvents, such as toluene and xylene; ether solvents, such as diethyl ether, tetrahydrofuran, diisopropyl ether, methyl t-butyl ether, dioxane, dimethoxyethane, diglyme, phenetole, 1,1-dimethoxy cyclohexane, and diisoamyl ether; and amide solvents, such as N,N-dimethylformamide, N,N-dimethylacetamide, N-methylpyrrolidone, 1,3-dimethyl-2-imidazolidinone, N,N-dimethylacrylamide, N,N-dimethylacetoacetamide, N,N-diethylformamide, and N,N-diethylacetamide.

The solvent is preferably inert to the starting material compound, the catalyst, and the product in step A.

When the α-fluoroacrylic acid compound (1) has a low boiling point, the solvent for use is preferably an organic solvent having a high boiling point (e.g., 100° C. or higher, more preferably 120° C. or higher) from the standpoint of ease of compound purification. The use of such an organic solvent enables purification of the α-fluoroacrylic acid compound (1) simply by distillation.

When the α-fluoroacrylic acid compound (1) has a high boiling point, the use of a solvent having a low boiling point suitably enables purification of the α-fluoroacrylic acid compound (1).

The amount of the solvent for use is not limited as long as part or all of the starting materials are dissolved at the reaction temperature. For example, the solvent is used in an amount of 0.2 to 50 parts by weight or 0.5 to 30 parts by weight per part by weight of the chlorofluoroethylene compound (2).

Step A is preferably performed in the absence of water. Specifically, the "absence of water" can mean that the amount of water is 2000 ppm or less.

The compound or reagent (e.g., a base such as an amine), and the solvent (which includes the alcohol (3), which can also serve as a solvent) all possibly containing water and used in step A are preferably dried before use.

The drying treatment can be performed, for example, by using a distillation technique, a dehydrating agent such as a molecular sieve, a commercially available dehydrated solvent, or a combination thereof.

The use of a compound or reagent and/or a solvent that is not dried may reduce the yield and selectivity of the desired product (i.e., α-fluoroacrylic acid compound) because of the generation of α-fluoroacrylic acids as by-products.

Reaction Time

The reaction time for the reaction can be determined, for example, on the basis of the desired starting material conversion and desired yield. Specifically, the reaction time is usually 1 to 48 hours, and preferably 5 to 30 hours.

The reaction time can be shortened by applying a higher reaction temperature.

Conversion and Yield

According to the production method of the present invention, for example, when a small amount of Pd is used (e.g., 0.025 mol %), the conversion of the starting material may be preferably 65% or more, more preferably 75% or more, and still more preferably 85% or more.

According to the production method of the present invention, for example, when a small amount of Pd is used (e.g., 0.025 mol %), the yield of the α-fluoroacrylic acid ester compound (1e) may be preferably 60% or more, more preferably 70% or more, and still more preferably 80% or more.

According to the production method of the present invention, an α-fluoroacrylic acid compound and/or a salt thereof, and an alcohol adduct of α-fluoroacrylic acid ester compound can be produced, together with the α-fluoroacrylic acid ester compound (1e).

According to the production method of the present invention, when a small amount of Pd is used (e.g., 0.025 mol %), the NMR yield of the α-fluoroacrylic acid compound may be within the range of 2 to 6%. According to the production method of the present invention, when a small amount of Pd is used (e.g., 0.025 mol %), the NMR yield of the alcohol adduct of the α-fluoroacrylic acid ester compound may be within the range of 0.05 to 0.2%.

Therefore, the present invention also provides a composition comprising

[1] the α-fluoroacrylic acid ester compound (1e); and
[2] a by-product-compound selected from the group consisting of the α-fluoroacrylic acid compound (1) (i.e., the α-fluoroacrylic acid compound described above and/or a salt thereof) and the alcohol adduct of the α-fluoroacrylic acid ester compound (1e).

The "α-fluoroacrylic acid compound" in terms of the "α-fluoroacrylic acid compound and/or a salt thereof" may be an a-fluoroacrylic acid compound represented by the formula:

wherein
$R^1$ and $R^2$ are identical or different, and each represents an alkyl group, a fluoroalkyl group, an aryl group optionally having one or more substituents, a halogen atom, or a hydrogen atom.

The salts thereof include metal salts (e.g., sodium salts, potassium salts), ammonium salts, and imidazole salts, as understood from the above description.

The alcohol adduct may be represented by $R^3O$—$R^1R^2C$—$CHF$—$CO_2$—$R^3$,
wherein
$R^1$ and $R^2$ are identical or different, and each represents an alkyl group, a fluoroalkyl group, an aryl group optionally having one or more substituents, a halogen atom, or a hydrogen atom; and
$R^3$ is an alkyl group, a fluoroalkyl group, or an aryl group optionally having one or more substituents.

The amount ratio of the α-fluoroacrylic acid ester compound (1) and the by-product compound in the composition may be, for example, in the range of 5:1 to 90:1, in the range of 9:1 to 70:1, or in the range of 15:1 to 50:1.

Purification

The α-fluoroacrylic acid ester compound (1) obtained by the production method of the present invention may optionally be purified by a known purification method, such as solvent extraction, desiccation, filtration, distillation, concentration, washing (e.g., washing with water), and a combination thereof.

The purification does not necessarily require complete removal of substances other than the α-fluoroacrylic acid ester compound (1) (hereinafter simply referred to as "other substances"). From the viewpoint of cost effectiveness, the other substances may be removed to an extent that the inconvenience caused by the other substances can be resolved to a desired degree.

Further, if it is desirable to maintain the other substances due to their type and function, purification may intentionally be performed under conditions in which the substances will remain.

These other substances may be a substance produced by the production method of the present invention or may be a substance intentionally or unintentionally added to the reaction system (e.g., a solvent) in the production method of the present invention. Examples of the other substances include water and aldehydes.

For example, for removing water, the purification can be performed, for example, by using a zeolite.

For example, for removing aldehydes, the purification may be performed, for example, by using at least one aminated carrier selected from the group consisting of a-fluoroacrylic amino-modified silica gel, amino-modified siloxane, and amino-modified acrylic resin, or by bringing sulfites or a compound having one or more amino groups into contact.

Each of these preferable examples of purification may be performed alone or in combination, as long as the effect of the present invention and the effect of the purification methods are not significantly impaired.

In particular, since the production method of the present invention generates only an extremely small amount of by-products and decomposed products, an extremely high-purity a-fluoroacrylic acid ester compound (1) can be obtained by a simple method such as distillation.

Composition (S)

The present invention also provides a composition (S) comprising

[1] an α-fluoroacrylic acid ester compound (1); and
[2] two or more members selected from the group consisting of alcohols, amides, and aldehydes.

In the composition (S), the α-fluoroacrylic acid ester compound (1) may be present stably.

Alcohol Contained in Composition (S)

The alcohol may be partly or entirely derived from the alcohol (3).

The alcohol contained in the composition (S) is preferably an alcohol having 1 to 6 carbon atoms.

Specific examples of the alcohol contained in the composition (S) include methanol, ethanol, n-propanol, isopropanol, n-butanol, isobutanol, tert-butanol, pentanol, and hexanol.

The alcohol contained in the composition (S) is particularly preferably methanol.

In the present invention, the alcohols can be used alone, or in a combination of two or more.

The lower limit of the alcohol content in the composition (S) is preferably 0.02% (w/w), more preferably 0.03% (w/w), still more preferably 0.1% (w/w), even more preferably 0.3% (w/w), particularly preferably 0.5% (w/w), more particularly preferably 1% (w/w), 1.5% (w/w), or 2.0%. (w/w), particularly preferably 3.0%, and more particularly preferably 5.0% (w/w).

For the purpose of stabilizing the α-fluoroacrylic acid ester compound (1), the upper limit of the alcohol content in the composition (S) is not limited; however, it is disadvantageous in terms of cost to use alcohol in an amount exceeding the amount at which the desired stabilization effect of the α-fluoroacrylic acid ester compound (1) is achieved. Therefore, the upper limit of the alcohol content in the composition (S) may be usually, for example, 70% (w/w), 50% (w/w), 40% (w/w), or 30% (w/w), 20% (w/w), 15% (w/w), 10% (w/w), 7% (w/w), 6% (w/w), 5% (w/w), 4% (w/w), or 3% (w/w).

The alcohol content in the composition (S) is preferably 0.01 to 70% (w/w), 0.01 to 50% (w/w), or 0.02 to 6% (w/w), more preferably 0.03 to 5% (w/w), still more preferably 0.1 to 4% (w/w), even more preferably 0.3 to 3.5 (w/w), particularly preferably 0.5 to 3% (w/w), and more particularly preferably 1 to 3% (w/w).

In the composition (S), the lower limit of the amount ratio of alcohol to the α-fluoroacrylic acid ester compound (1) (i.e., the ratio of alcohol/α-fluoroacrylic acid ester compound (1)) is preferably 0.02% (w/w), more preferably 0.03% (w/w), still more preferably 0.1% (w/w), even more preferably 0.3% (w/w), particularly preferably 0.5% (w/w), and more particularly preferably 1% (w/w).

For the purpose of stabilizing the α-fluoroacrylic acid ester compound (1), the upper limit of the amount ratio of alcohol to the α-fluoroacrylic acid ester compound (1) (i.e., the ratio of alcohol/α-fluoroacrylic acid ester compound (1)) is not limited, however, it is disadvantageous in terms of cost to use alcohol in an amount exceeding the amount at which the desired stabilization effect of the α-fluoroacrylic acid ester compound (1) is achieved. Therefore, the upper limit of the amount ratio of alcohol to the α-fluoroacrylic acid ester compound (1) (i.e., the ratio of alcohol/α-fluoroacrylic acid ester compound (1)) may be usually, for example, 200% (w/w), 190% (w/w), 170% (w/w), 150% (w/w), 100% (w/w), 70% (w/w), 50% (w/w), 40% (w/w), or 30% (w/w), 20% (w/w), 15% (w/w), 10% (w/w), 7% (w/w), 6% (w/w), 5% (w/w), 4% (w/w), or 3% (w/w).

In the composition (S), the amount ratio of alcohol to α-fluoroacrylic acid ester compound (1) is preferably 0.01 to 200% (w/w), 0.01 to 190% (w/w), 0.01 to 170% (w/w), 0.01 to 100% (w/w), or 0.02 to 6% (w/w), more preferably 0.03 to 5% (w/w), still more preferably 0.1 to 4% (w/w), even more preferably 0.3 to 3.5% (w/w), particularly preferably 0.5 to 3% (w/w), and more particularly preferably 1 to 3% (w/w).

Amide Contained in Composition (S)

Specific examples of the amide contained in the composition (S) include N,N-dimethylformamide (DMF), N,N-dimethylacetamide (DMAC), N-methylpyrrolidone, 1,3-dimethyl-2-imidazolidinone, N,N-dimethylacrylamide, N,N-dimethylacetamide, N,N-diethylformamide, and N,N-diethylacetamide.

The amide contained in the composition (S) is preferably represented by formula: $R^{10}R^{11}$—N—CO—$R^{12}$ (wherein $R^{10}$ and $R^{11}$ represent an alkyl group having 1 to 3 carbon atoms, and $R^{12}$ is a hydrogen atom or an alkyl group having 1 to 3 carbon atoms).

The amide contained in the composition (S) is preferably an amide having 3 to 8 carbon atoms.

The amide contained in the composition (S) is particularly preferably N,N-dimethylformamide or N,N-dimethylacetamide.

In the present invention, the amides can be used alone, or in a combination of two or more.

The lower limit of the content of the amide in the composition (S) is preferably 0.01% (w/w), 0.05% (w/w), 0.1% (w/w), 0.5% (w/w), or 1.0% (w/w), more preferably 3.0% (w/w), and still more preferably 5.0% (w/w).

For the purpose of stabilizing the α-fluoroacrylic acid ester compound (1), the upper limit of the content of the amide in the composition (S) is not limited; however, it is disadvantageous in terms of cost to use the amide in an amount exceeding the amount at which the desired stabilization effect of the α-fluoroacrylic acid ester compound (1) is achieved. Therefore, the upper limit of the content of the amide in the composition (S) may be usually, for example, 50% (w/w), 40% (w/w), 30% (w/w), 20% (w/w), or 10% (w/w).

The content of the amide in the composition (S) is preferably 0.01 to 50% (w/w), more preferably 1.0 to 40% (w/w), still more preferably 5.0 to 30% (w/w), and even more preferably 1 to 3% (w/w).

In the composition (S), the lower limit of the amount ratio of the amide to the α-fluoroacrylic acid ester compound (1) (i.e., the ratio of amide/α-fluoroacrylic acid ester compound (1)) is preferably 0.01% (w/w) or 0.05% (w/w), more preferably 0.1% (w/w), still more preferably 0.5% (w/w), even more preferably 1.0% (w/w), particularly preferably 3.0% (w/w), and more particularly preferably 5.0% (w/w).

For the purpose of stabilizing the α-fluoroacrylic acid ester compound (1), the upper limit of the amount ratio of the amide to the α-fluoroacrylic acid ester compound (1) (i.e., the ratio of the amide/α-fluoroacrylic acid ester compound (1)) is not limited; however, it is disadvantageous in terms of cost to use the amide in an amount exceeding the amount at which the desired stabilization effect of the α-fluoroacrylic acid ester compound (1) is achieved. Therefore, the upper limit of the amount ratio of the amide to the α-fluoroacrylic acid ester compound (1) (i.e., the ratio of amide/α-fluoroacrylic acid ester compound (1)) may be usually, for example, 200% (w/w), 190% (w/w), 170% (w/w), 150% (w/w), 100% (w/w) 70% (w/w), 50% (w/w), 40% (w/w), or 30% (w/w).

In the composition (S), the amount ratio of the amide to the α-fluoroacrylic acid ester compound (1) is preferably 0.01 to 200% (w/w), more preferably 0.1 to 190% (w/w), still more preferably 1 to 170% (w/w), even more preferably 3 to 50% (w/w), and particularly preferably 5 to 50% (w/w).

Aldehyde Contained in Composition (S) The aldehyde may be at least one member selected from the group consisting of aliphatic aldehydes, and aromatic aldehydes optionally substituted with at least one substituent.

The "aliphatic aldehyde" may be a linear or branched aliphatic aldehyde, and may be a saturated or unsaturated aliphatic aldehyde.

The aldehyde is preferably linear saturated aldehyde having 1 to 20 (preferably 1 to 12, more preferably 1 to 6, still more preferably 1 to 4, even more preferably 1 to 3, and particularly preferably 1 or 2) carbon atoms.

The "aliphatic aldehyde" refers to, for example, a compound represented by formula: R—CHO, wherein R is an aliphatic hydrocarbon group. The aliphatic hydrocarbon group represented by R is preferably an aliphatic hydrocarbon group.

In the present specification, "aromatic aldehyde" refers to, for example, a compound represented by formula: R—CHO, wherein R is aryl optionally substituted with at least one substituent (e.g., alkyl group).

Specifically, the aldehyde is preferably one or more members (preferably one member) selected from the group consisting of formaldehyde, acetaldehyde, n-propylaldehyde, isopropylaldehyde, n-butylaldehyde, isobutylaldehyde, pivalaldehyde, n-pentylaldehyde, n-hexylaldehyde, n-heptylaldehyde, n-octylaldehyde, nonylaldehyde, decylaldehyde, undecylaldehyde, dodecylaldehyde, tridecylaldehyde, benzaldehyde, o-anisaldehyde, m-anisaldehyde, p-anisaldehyde, o-tolualdehyde, m-tolualdehyde, and p-tolualdehyde, and more preferably n-butylaldehyde.

The aldehyde may be produced by a known method or a method in accordance with the known method, or may be obtained from commercial suppliers.

In the composition (S), the content of the aldehyde is preferably 0.1 mol or less, more preferably 0.05 mol or less, and further preferably 0.02 mol or less, per mole of the α-fluoroacrylic acid ester compound (1).

In the composition (S), even a very small amount of the aldehyde can stabilize the α-fluoroacrylic acid ester compound (1); however, in the composition (S), the content of the aldehyde is, for example, 0.0005 mol or more per mole of the α-fluoroacrylic acid ester compound (1).

In the composition (S), the molar ratio of the α-fluoroacrylic acid ester compound (1) and the aldehyde is preferably 1:0.1 or less, more preferably 1:0.0005 to 1:0.05, and still more preferably 1:0.0005 to 1:0.02.

In the composition (S), the amount ratio of the alcohol, the amide, and the aldehyde is not limited.

The present invention also provides an α-fluoroacrylic acid ester compound (1) in which the α-fluoroacrylic acid ester compound (1) and [2] two or more members selected from the group consisting of alcohols, amides, and aldehydes are present together. The method can be understood from the description of the composition (S).

EXAMPLES

The present invention is described in more detail below with reference to Examples; however, the present invention is not limited to these Examples.

In the Examples, "yield" can represent "NMR yield," unless otherwise specified.

Comparative Example 1

1-Chloro-1-fluoroethene (1.61 g), triethylamine (2.23 g), dichloro[1,1-bis(diisopropylphosphino)ferrocene]palladium (II) (9.0 mg), and methanol (16 g) were placed in an autoclave. Carbon monoxide (0.6 MPaG) was introduced thereinto, followed by stirring at 100° C. for 7 hours.

The unreacted gas was purged; and the reaction liquid in the autoclave was quantified based on $^{19}$F-NMR integral values, which revealed that the amount of 2-fluoroacrylic acid methyl ester was 1.28 g (yield: 61.5%, selectivity: 96.6%), the yield of 2-fluoroacrylate was 2.2%, and the amount of unreacted 1-chloro-1-fluoroethene was 0.52 g (recovery rate: 32.0%).

Example 1

1-Chloro-1-fluoroethene (1.61 g), triethylamine (2.23 g), bis(acetylacetonato)palladium (II) (4.6 mg), 1,1'-bis(diisopropylphosphino)ferrocene (6.3 mg), and methanol (16 g) were placed in an autoclave. Carbon monoxide (0.6 MPaG) was introduced thereinto, followed by stirring at 100° C. for 7 hours.

The unreacted gas was purged; and the reaction liquid in the autoclave was quantified based on $^{19}$F-NMR integral values, which revealed that the amount of 2-fluoroacrylic acid methyl ester was 1.75 g (yield: 84%, selectivity: 91%), the yield of 2-fluoroacrylate was 2.3%, and the amount of unreacted 1-chloro-1-fluoroethene was 0.13 g (recovery rate: 8%).

Example 2

1-Chloro-1-fluoroethene (1.61 g), triethylamine (2.23 g), dichloro(1,5-cyclooctadiene)palladium (II) (4.2 mg), 1,1'-bis(diisopropylphosphino)ferrocene (6.3 mg), and methanol (16 g) were placed in an autoclave. Carbon monoxide (0.6 MPaG) was introduced thereinto, followed by stirring at 100° C. for 7 hours.

The unreacted gas was purged; and the reaction liquid in the autoclave was quantified based on $^{19}$F-NMR integral values, which revealed that the amount of 2-fluoroacrylic acid methyl ester was 1.38 g (yield: 66.3%, selectivity: 96.6%), and the yield of 2-fluoroacrylate was 2.3%, and the amount of unreacted 1-chloro-1-fluoroethene was 0.40 g (recovery rate: 24.6%).

Comparative Example 2

1-Chloro-1-fluoroethene (1.61 g), triethylamine (2.23 g), dichloro[1,1-bis(diisopropylphosphino)ferrocene]palladium (II) (3.0 mg), and methanol (16 g) were placed in an autoclave. Carbon monoxide (0.6 MPaG) was introduced thereinto, followed by stirring at 100° C. for 18 hours.

The unreacted gas was purged; and the reaction liquid in the autoclave was quantified based on $^{19}$F-NMR integral values, which revealed that the amount of 2-fluoroacrylic acid methyl ester was 0.59 g (yield: 28.2%, selectivity: 91.4%), and the yield of 2-fluoroacrylate was 2.7%, and the amount of unreacted 1-chloro-1-fluoroethene was 0.61 g (recovery rate: 37.8%).

Example 3

1-Chloro-1-fluoroethene (1.61 g), triethylamine (2.23 g), bis(dibenzylideneacetone)palladium (0) (17.3 mg), 1,1'-bis(diisopropylphosphino)ferrocene (12.6 mg), and methanol (16 g) were placed in an autoclave. Carbon monoxide (0.65 MPaG) was introduced thereinto, followed by stirring at 100° C. for 7 hours.

The unreacted gas was purged; and the reaction liquid in the autoclave was quantified based on $^{19}$F-NMR integral values, which revealed that the amount of 2-fluoroacrylic acid methyl ester was 1.35 g (yield: 65%, selectivity: 96%), the yield of 2-fluoroacrylate was 2.5%, and the amount of unreacted 1-chloro-1-fluoroethene was 0.21 g (recovery rate: 13%).

Comparative Example 3

1-Chloro-1-fluoroethene (1.61 g), triethylamine (2.23 g), dichloro[1,1-bis(diisopropylphosphino)ferrocene]palladium (II) (18.0 mg), and methanol (16 g) were placed in an autoclave. Carbon monoxide (0.65 MPaG) was introduced thereinto, followed by stirring at 100° C. for 7 hours.

The unreacted gas was purged; and the reaction liquid in the autoclave was quantified based on $^{19}$F-NMR integral values, which revealed that the amount of 2-fluoroacrylic acid methyl ester was 0.96 g (yield: 46%, selectivity: 94%), the yield of 2-fluoroacrylate was 2.7%, and the amount of unreacted 1-chloro-1-fluoroethene was 0.37 g (recovery rate: 23%).

Example 4

1-Chloro-1-fluoroethene (3.22 g), triethylamine (4.45 g), bis(acetylacetonato)palladium (II) (3.0 mg), 1,1'-bis(diisopropylphosphino)ferrocene (4.2 mg), and methanol (32 g) were placed in an autoclave. Carbon monoxide (0.65 MPaG) was introduced thereinto, followed by stirring at 100° C. for 22 hours.

The unreacted gas was purged; and the reaction liquid in the autoclave was quantified based on $^{19}$F-NMR integral values, which revealed that the amount of 2-fluoroacrylic acid methyl ester was 3.04 g (yield: 73%, selectivity: 88%), and the yield of 2-fluoroacrylate was 3.9%, and the amount of unreacted 1-chloro-1-fluoroethene was 0.55 g (recovery rate: 17%).

Example 5

1-Chloro-1-fluoroethene (1.61 g), triethylamine (2.23 g), bis(acetylacetonato)palladium (II) (4.6 mg), 1,3-bis(dicyclohexylphosphino)propane (6.5 mg), and methanol (16 g) were placed in an autoclave. Carbon monoxide (0.65 MPaG) was introduced thereinto, followed by stirring at 100° C. for 7 hours.

Example 6

1-Chloro-1-fluoroethene (1.61 g), triethylamine (2.23 g), bis(acetylacetonato)palladium (II) (4.6 mg), bis(dicyclohexylphosphinophenyl)ether (9.0 mg), and methanol (16 g) were placed in an autoclave. Carbon monoxide (0.65 MPaG) was introduced thereinto, followed by stirring at 100° C. for 7 hours.

The unreacted gas was purged; and the reaction liquid in the autoclave was quantified based on $^{19}$F-NMR integral values, which revealed that the amount of 2-fluoroacrylic acid methyl ester was 1.48 g (yield: 71%, selectivity: 97%), the yield of 2-fluoroacrylate was 2.5%, and the amount of unreacted 1-chloro-1-fluoroethene was 0.24 g (recovery rate: 15%).

Example 7

1-Chloro-1-fluoroethene (3.22 g), triethylamine (4.45 g), bis(acetylacetonato)palladium (II) (3.0 mg), 1,4-bis(dicyclohexylphosphino)butane (4.5 mg), and methanol (32 g) were placed in an autoclave. Carbon monoxide (0.65 MPaG) was introduced thereinto, followed by stirring at 100° C. for 20 hours.

The unreacted gas was purged; and the reaction liquid in the autoclave was quantified based on $^{19}$F-NMR integral values, which revealed that the amount of 2-fluoroacrylic acid methyl ester was 3.75 g (yield: 90%, selectivity: 95%), the yield of 2-fluoroacrylate was 5.9%, the yield of 2-fluoro-3-methoxypropionic acid methyl ester was 0.1%, and the amount of unreacted 1-chloro-1-fluoroethene was 0.16 g (recovery rate: 5%).

Example 8

1-Chloro-1-fluoroethene (3.22 g), triethylamine (4.45 g), bis(acetylacetonato)palladium (II) (3.0 mg), 1,1'-bis(diisopropylphosphino)ferrocene (4.2 mg), 2,4-pentanedione (1.0 mg), and methanol (32 g) were placed in an autoclave. Carbon monoxide (0.65 MPaG) was introduced thereinto, followed by stirring at 100° C. for 12 hours.

The unreacted gas was purged; and the reaction liquid in the autoclave was quantified based on $^{19}$F-NMR integral values, which revealed that the amount of 2-fluoroacrylic acid methyl ester was 2.88 g (yield: 69%, selectivity: 96%), the yield of 2-fluoroacrylate was 2.7%, and the amount of unreacted 1-chloro-1-fluoroethene was 0.93 g (recovery rate: 29%).

Example 9

1-Chloro-1-fluoroethene (3.22 g), triethylamine (4.45 g), dichloro(1,5-cyclooctadiene)palladium (II) (2.9 mg), 1,1'-bis(diisopropylphosphino)ferrocene (4.2 mg), 1,5-cyclooctadiene (1.1 mg), and methanol (32 g) were placed in an autoclave. Carbon monoxide (0.65 MPaG) was introduced thereinto, followed by stirring at 100° C. for 21 hours.

The unreacted gas was purged; and the reaction liquid in the autoclave was quantified based on $^{19}$F-NMR integral values, which revealed that the amount of 2-fluoroacrylic acid methyl ester was 2.81 g (yield: 67%, selectivity: 86%), the yield of 2-fluoroacrylate was 4.6%, and the amount of unreacted 1-chloro-1-fluoroethene was 0.60 g (recovery rate: 19%).

Example 10

1-Chloro-1-fluoroethene (4.81 g), triethylamine (6.68 g), bis(acetylacetonato)palladium (II) (4.6 mg), 1,4-bis(dicyclohexylphosphino)butane (6.8 mg), 2,4-pentanedione (1.5 mg), and methanol (48 g) were placed in an autoclave. Carbon monoxide (0.65 MPaG) was introduced thereinto, followed by stirring at 100° C. for 22 hours.

The unreacted gas was purged; and the reaction liquid in the autoclave was quantified based on $^{19}$F-NMR integral values, which revealed that the amount of 2-fluoroacrylic acid methyl ester was 4.41 g (yield: 71%, selectivity: 91%), the yield of 2-fluoroacrylate was 5.1%, and the amount of unreacted 1-chloro-1-fluoroethene was 0.58 g (recovery rate: 12%).

Example 11

1-Chloro-1-fluoroethene (6.04 g), triethylamine (8.35 g), bis(acetylacetonato)palladium (II) (11.4 mg), 1,1'-bis(dicyclohexylphosphino)ferrocene bis(tetrafluoroborate) (22.3 mg), and methanol (33 g) were placed in an autoclave. Carbon monoxide (0.75 MPaG) was introduced thereinto, followed by stirring at 90° C. for 24 hours.

The unreacted gas was purged; and the reaction liquid in the autoclave was quantified based on $^{19}$F-NMR integral values, which revealed that the amount of 2-fluoroacrylic acid methyl ester was 5.93 g (yield: 76%, selectivity: 92%), the yield of 2-fluoroacrylate was 3.6%, and the amount of unreacted 1-chloro-1-fluoroethene was 1.04 g (recovery rate: 17%).

Example 12

1-Chloro-1-fluoroethene (6.04 g), triethylamine (8.35 g), bis(acetylacetonato)palladium (II) (11.4 mg), 1,4-bis(dicyclohexylphosphino)butane bis(tetrafluoroborate) (23.5 mg), and methanol (33 g) were placed in an autoclave. Carbon monoxide (0.75 MPaG) was introduced thereinto, followed by stirring at 90° C. for 24 hours.

The unreacted gas was purged; and the reaction liquid in the autoclave was quantified based on $^{19}$F-NMR integral values, which revealed that the amount of 2-fluoroacrylic acid methyl ester was 7.26 g (yield: 93%, selectivity: 94%), the yield of 2-fluoroacrylate was 4.6%, and the remaining percentage of unreacted 1-chloro-1-fluoroethene was 1.4%.

Example 13

1-Chloro-1-fluoroethene (1.61 g), triethylamine (2.23 g), bis(acetylacetonato)palladium (II) (3.0 mg), 1,4-bis(dicyclohexylphosphino)butane (4.5 mg), dibutyl hydroxytoluene (42 mg), and methanol (11 g) were placed in an autoclave. Carbon monoxide (0.70 MPaG) was introduced thereinto, followed by stirring at 100° C. for 21 hours.

The unreacted gas was purged; and the reaction liquid in the autoclave was quantified based on $^{19}$F-NMR integral values, which revealed that the amount of 2-fluoroacrylic acid methyl ester was 1.73 g (yield: 86%, selectivity: 90%), the yield of 2-fluoroacrylate was 9.3%, the yield of 2-fluoro- 3-methoxypropionic acid methyl ester was 0.6%, and the remaining percentage of unreacted 1-chloro-1-fluoroethene was 0.1%.

Example 14

The reaction liquid obtained in Example 8 was purified by simple distillation; and the obtained distillate was analyzed by gas chromatography, which revealed that 2-fluoroacrylic acid methyl ester was contained in an amount of 79.9 area %, methanol in an amount of 18.8 area %, triethylamine in an amount of 1.2 area %, and methyl acetate in an amount of 0.08 area %.

Example 15

1-Chloro-1-fluoroethene (4.82 g), triethylamine (6.68 g), bis(acetylacetonato)palladium (II) (9.1 mg), 1,4-bis(dicyclohexylphosphino)butane (13.5 mg), and methanol (34 g) were placed in an autoclave. Carbon monoxide (0.75 MPaG) was introduced thereinto, followed by stirring at 90° C. for 22 hours.

The unreacted gas was purged; and the reaction liquid in the autoclave was quantified based on $^{19}$F-NMR integral values, which revealed that the amount of 2-fluoroacrylic acid methyl ester was 5.69 g (yield: 91%, selectivity: 97%), the yield of 2-fluoroacrylate was 2.6%, and the remaining percentage of unreacted 1-chloro-1-fluoroethene was 0.5%.

Example 16

1-Chloro-1-fluoroethene (4.82 g), triethylamine (6.68 g), bis(acetylacetonato)palladium (II) (9.1 mg), 1,4-bis(dicyclohexylphosphino)butane (13.5 mg), and methanol (29 g) were placed in an autoclave. Carbon monoxide (0.75 MPaG) was introduced thereinto, followed by stirring at 85° C. for 22 hours.

The unreacted gas was purged; and the reaction liquid in the autoclave was quantified based on $^{19}$F-NMR integral values, which revealed that the amount of 2-fluoroacrylic acid methyl ester was 5.81 g (yield: 93%, selectivity: 97%), the yield of 2-fluoroacrylate was 2.9%, and the remaining percentage of unreacted 1-chloro-1-fluoroethene was 0.5%.

Example 17

1-Chloro-1-fluoroethene (6.44 g), triethylamine (8.90 g), bis(acetylacetonato)palladium (II) (12.2 mg), 1,4-bis (dicyclohexylphosphino)butane (18.0 mg), and methanol (32 g) were placed in an autoclave. Carbon monoxide (0.75 MPaG) was introduced thereinto, followed by stirring at 85° C. for 26 hours.

The unreacted gas was purged; and the reaction liquid in the autoclave was quantified based on $^{19}$F-NMR integral values, which revealed that the amount of the 2-fluoroacrylic acid methyl ester was 7.58 g (yield: 91%, selectivity: 94%), the yield of 2-fluoroacrylate was 5.5%, and the remaining percentage of unreacted 1-chloro-1-fluoroethene was 2.2%.

Example 18

1-Chloro-1-fluoroethene (6.04 g), triethylamine (8.35 g), bis(acetylacetonato)palladium (II) (11.4 mg), 1,4-bis(dicyclohexylphosphino)butane (16.9 mg), and methanol (33 g) were placed in an autoclave. Carbon monoxide (0.75 MPaG) was introduced thereinto, followed by stirring at 90° C. for 24 hours.

The unreacted gas was purged; and the reaction liquid in the autoclave was quantified based on $^{19}$F-NMR integral values, which revealed that the amount of 2-fluoroacrylic acid methyl ester was 7.26 g (yield: 93%, selectivity: 96%), the yield of 2-fluoroacrylate was 4.1%, and the remaining percentage of unreacted 1-chloro-1-fluoroethene was 0.7%.

Example 19 n-Butyl aldehyde (0.1 g) was added to 48.5 g of the reaction liquid obtained in Example 15, and the mixture was subjected to simple distillation. The fraction was collected in a receiver into which 3.0 g of N,N-dimethylacetamide was placed beforehand, thus obtaining 34.4 g of a fraction. The fraction was analyzed by gas chromatography, which revealed that 2-fluoroacrylic acid methyl ester was contained in an amount of 19.2 area %, methanol in an amount of 68.7 area %, triethylamine in an amount of 2.45 area %, N,N-dimethylacetamide in an amount of 3.74 area %, and n-butyl aldehyde in an amount of 0.24%.

INDUSTRIAL APPLICABILITY

The present invention is capable of producing an α-fluoroacrylic acid ester compound that is useful as a synthetic intermediate at a high starting material conversion and a high yield.

The invention claimed is:

1. A method for producing a compound represented by formula (1) or a salt thereof:

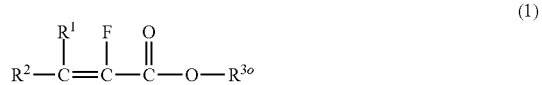

wherein
$R^1$ and $R^2$ are identical or different, and each represents an alkyl group, a fluoroalkyl group, an aryl group optionally having one or more substituents, a halogen atom, or a hydrogen atom;
$R^{3o}$ is a hydrogen atom or $R^3$; and
$R^3$ is an alkyl group, a fluoroalkyl group, or an aryl group optionally having one or more substituents,
the method comprising step A of reacting a compound represented by formula (2):

wherein the symbols in the formula are as defined above, with carbon monoxide and an alcohol represented by formula (3):

wherein the symbol in the formula is as defined above,
in the presence of
palladium,
a double bond-containing compound (α) represented by formula (α):

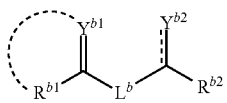 (α)

wherein
$R^{b1}$ is a hydrogen atom or a $C_{1-6}$ alkyl group,
$R^{b2}$ is a hydrogen atom or a $C_{1-6}$ alkyl group,
$Y^{b1}$ is =O or =CH—$R^{yb1}$,
$Y^{b2}$ is —H, =O or =CH—$R^{yb2}$,
$R^{yb1}$ is a hydrogen atom or a $C_{6-14}$ aryl group,
$R^{yb2}$ is a $C_{6-14}$ aryl group,
or
$R^{b1}$ and $Y^{b1}$, taken together with the adjacent carbon atom, may form an aromatic hydrocarbon ring,
$L^b$ is a bond, $C_{1-3}$ alkanediyl optionally having one or more side chains, or —C(=O)—,
or
$R^{yb1}$ and $R^{yb2}$ may be linked to each other to form -$L^y$-, wherein $L^y$ is linear
$C_{1-2}$ alkanediyl optionally having one or more side chains, wherein one of the side chains in $L^b$
(1) may be linked to one of the side chains in $L^y$ to form linear $C_{1-2}$ hydrocarbon diyl, or
(2) may be linked to $R^{b1}$ to form $C_{3-4}$ alkanediyl,
a diphosphine compound (β) having, on each phosphorus atom, at least one substituent selected from the group consisting of alkyl and cycloalkyl groups, and a base, with the proviso that, in the reaction, the palladium, taken together with the compound represented by formula (2), the double bond-containing compound (α), the diphosphine compound (β), or carbon monoxide, or with one or more of these, may form a palladium complex (A),
to obtain the compound represented by formula (1) or a salt thereof.

2. The method according to claim 1, wherein $R^1$ and $R^2$ each represent a hydrogen atom.

3. The method according to claim 1, wherein $R^{yb1}$ is a $C_{6-14}$ aryl group.

4. The method according to claim 1, wherein
$Y^{b1}$ is =O,
$Y^{b2}$ is =O, and
$L^b$ is methanediyl optionally having a side chain.

5. The method according to claim 1, wherein
$Y^{b1}$ is =CH—$R^{yb1}$,
$Y^{b2}$ is =CH—$R^{yb2}$, and
$L^b$ is a bond, —C(=O)—, methanediyl, or 1,2-ethanediyl.

6. The method according to claim 1, wherein
$R^{b1}$ is a hydrogen atom,
$Y^{b1}$ is =CH—$R^{yb1}$,
$Y^{b2}$ is a hydrogen atom, and
$L^b$ is a bond.

7. The method according to claim 1, wherein the base is an amine.

8. The method according to claim 1, wherein step A is performed at a temperature of 20° C. or higher.

* * * * *